(12) United States Patent
Weimann

(10) Patent No.: US 11,867,984 B2
(45) Date of Patent: Jan. 9, 2024

(54) METHODS FOR DETERMINING THE NEAR POINT, FOR DETERMINING THE NEAR POINT DISTANCE, FOR DETERMINING A SPHERICAL REFRACTIVE POWER, AND FOR PRODUCING A SPECTACLE LENS, AND CORRESPONDING MOBILE TERMINALS AND COMPUTER PROGRAMS

(71) Applicant: Carl Zeiss Vision International GmbH, Aalen (DE)

(72) Inventor: Claudius Weimann, Böbingen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/157,454

(22) Filed: Jan. 20, 2023

(65) Prior Publication Data

US 2023/0152604 A1 May 18, 2023

Related U.S. Application Data

(63) Continuation of application No. PCT/EP2021/071167, filed on Jul. 28, 2021.

(30) Foreign Application Priority Data

Jul. 29, 2020 (EP) .................................... 20188386

(51) Int. Cl.
*G02C 7/02* (2006.01)
*A61B 3/032* (2006.01)
(Continued)

(52) U.S. Cl.
CPC .............. *G02C 7/027* (2013.01); *A61B 3/032* (2013.01); *A61B 3/10* (2013.01); *A61B 5/6898* (2013.01)

(58) Field of Classification Search
CPC .......... A61B 3/113; A61B 3/11; A61B 3/103; A61B 3/1005; A61B 3/10; A61B 3/0091;
(Continued)

(56) References Cited

U.S. PATENT DOCUMENTS 7,465,049 B2 * 12/2008 Maeda .................. A61B 3/152
351/205
9,395,562 B1 7/2016 Ngyuen et al.
(Continued)

FOREIGN PATENT DOCUMENTS

CN 107850793 A 3/2018
CN 108567406 A 9/2018
(Continued)

OTHER PUBLICATIONS

F. Donders, "On the anomalies of accommodation and refraction of the eye with a preliminary essay on physiological dioptrics," published by The New Sydenham Society, London, 1864.
(Continued)

*Primary Examiner* — Travis S Fissel
(74) *Attorney, Agent, or Firm* — Tautz & Schuhmacher LLC; Georg M. Hasselmann

(57) ABSTRACT

A method for determining a near point and a near point distance of a person is disclosed, as well as methods for determining a spherical refractive power. In one implementation, optotypes are displayed on a mobile terminal and the person is asked to move the mobile terminal to the near point of the person. The position of the mobile terminal is determined on the basis of images of the surroundings and measurements of an acceleration of the mobile terminal. The near point distance can then be determined from the position of the mobile terminal at the near point and a position of the eyes of the person. Corresponding computer programs and corresponding mobile terminals are also disclosed.

29 Claims, 7 Drawing Sheets

(51) Int. Cl.
  *A61B 3/10* (2006.01)
  *A61B 5/00* (2006.01)
(58) Field of Classification Search
  CPC ..... A61B 3/0066; A61B 3/0058; A61B 3/005;
    A61B 3/0041; A61B 3/0033; A61B
    3/0025; A61B 3/0016; A61B 3/0285;
    A61B 3/028; A61B 3/032; A61B 5/6898;
    G02C 7/028; G02C 7/025; G02C 7/024;
    G02C 7/027
  USPC .............................. 351/178, 159.73–159.77
  See application file for complete search history.

(56) References Cited

U.S. PATENT DOCUMENTS

| | | | |
|---|---|---|---|
| 10,702,148 | B2 | 7/2020 | Breuninger et al. |
| 2015/0094952 | A1* | 4/2015 | Moeglein ............... G01S 19/14 701/532 |
| 2016/0120402 | A1* | 5/2016 | Limon ................ A61B 3/0033 351/239 |
| 2017/0003519 | A1 | 1/2017 | Burkert et al. |
| 2017/0202450 | A1 | 7/2017 | Carrafa et al. |
| 2018/0116499 | A1* | 5/2018 | Singer .................. A61B 5/4064 |
| 2019/0246896 | A1 | 8/2019 | Hernandez-Castenada et al. |
| 2021/0165999 | A1* | 6/2021 | Mirbach .................. G06T 7/75 |

FOREIGN PATENT DOCUMENTS

| | | |
|---|---|---|
| WO | 2018002332 A2 | 1/2018 |
| WO | 2019157925 A1 | 8/2019 |

OTHER PUBLICATIONS

A. Duane, "Normal values of the accommodation at all ages," Journal of American Medical Association, vol. 59, No. 12, pp. 1010-1013, 1912.
B. Gilmartin, "The Marton Lecture: Ocular Manifestations of Systemic Medication," Ophthalmic and Physiological Optics, vol. 7, No. 4, pp. 449 459, 1987.
C. Braun et al., "Accommodative amplitudes in the Early Treatment Diabetic Retinopathy Study," Retina, vol. 15, No. 4, pp. 275-281, 1995.
G. Nützi et al., "Fusion of IMU and Vision for Absolute Scale Estimation in Monocular SLAM," Journal of Intelligent & Robotic Systems, vol. 61, pp. 287-299, 2011.
F. Timm et al., "Accurate eye center localization by means of gradients," Proceedings of the Int. Conference on Computer Theory and Applications (VISAPP), vol. 1, pp. 125-130, Portugal, 2011.
I. Takeshi et al., "New Compact Accommodometer to Measure Accommodation Amplitude as a Biomarker," The Asia-Pacific Journal of Ophthalmology, vol. 1, No. 1, pp. 24-27, 2012.
I. Takeshi et al., "The Effect of 3D Visual Simulator on Children's Visual Acuity—A Pilot Study Comparing Two Different Modalities", The Open Ophthalmology Journal, vol. 7, pp. 69-48, 2013.
A. Kingsnorth, "Technological enhancements to optometric clinical tests," Ph.D. dissertation, Aston University, Mar. 2015.
E. Salahat et al., "Recent advances in features extraction and description algorithms: A comprehensive survey," IEEE International Conference on Industrial Technology (ICIT), pp. 1059-1063, 2017.
Wikipedia entry "Direct linear transformation," available at https://en.wikipedia.org/wiki/Direct_linear_transformation, last edited Jun. 4, 2021, last accessed Jan. 20, 2023.
Wikipedia entry "Homogene Koordinaten [Homogeneous coordinates]," available at https://de.wikipedia.org/wiki/Homogene_Koordinaten, last edited Apr. 6, 2021, last accessed Jan. 16, 2023, and English-language counterpart entry thereof.
Wikipedia entry "Triangulation (Messtechnik)" [Triangulation (measuring technology)], available at https://de.wikipedia.org/wiki/Triangulation_(Messtechnik), last edited Feb. 13, 2022, last accessed Jan. 20, 2023.
N. Naja, "Amplitude of accommodation test," Online tutorial available at https://www.youtube.com/watch?v=JjrRtH0qk_0, uploaded Nov. 13, 2016, 10 sample screen shots submitted, last accessed Jan. 20, 2023.
Industrial Norm "Roboter und Robotikgeräte—Robots and robotic devices", German and English version EN ISO 8373:2012, Mar. 2012.
Industrial Norm "Ophthalmic optics—Spectacle lenses—Vocabulary," German and English version DIN EN ISO 13666:2013, Oct. 2013.
International Search Report issued in PCT/EP2021/071167, to which this application claims priority, dated Nov. 15, 2021, and English-language translation thereof.
Written Opinion issued in PCT/EP2021/071167, to which this application claims priority, dated Nov. 15, 2021.
Extended European Search Report issued in EP 20 188 386.5, to which this application claims priority, dated Jan. 13, 2021, and English-language translation thereof.
International Preliminary Examination Report issued in PCT/EP2021/071167, to which this application claims priority, dated Nov. 15, 2021, and English-language translation thereof.
Industrial Norm "Terms of physiological optics (DIN 5340:1998)," German and English version DIN 5340:1998, Apr. 1998.
Industrial Norm "Ergonomics—Human body dimensions—Part 2: Values (ISO 33402-2:2020)," German and English version DIN 33402-2:2020, Dec. 2020.
C. Sheard, "Dynamic Skiametry and Methods of Testing the Assommodation and Convergence of the Eyes," in Physiological Optics, pp. 1 to 108, Cleveland Press, Chicago, 1920.
Office Action by the Chinese Patent Office issued in CN 202180060121.3, which is a counterpart hereof, dated Jul. 31, 2023, and English translation thereof.

* cited by examiner

METHODS FOR DETERMINING THE NEAR POINT, FOR DETERMINING THE NEAR POINT DISTANCE, FOR DETERMINING A SPHERICAL REFRACTIVE POWER, AND FOR PRODUCING A SPECTACLE LENS, AND CORRESPONDING MOBILE TERMINALS AND COMPUTER PROGRAMS

CROSS REFERENCE TO RELATED APPLICATIONS

This application is a continuation application of international patent application PCT/EP2021/071167, filed on Jul. 28, 2021, designating the U.S. and claiming priority to European patent application EP 20 188 386.5, filed on Jul. 29, 2020, both of which are hereby incorporated by reference in their entireties.

TECHNICAL FIELD

The present patent application relates to methods and apparatuses, more particularly mobile terminals, for determining the near point and the near-point distance of a person. Moreover, the application relates to methods and devices for determining a spherical power, in particular for reading glasses or a near portion of varifocal spectacles, using the near-point distance determined in this way, and to a method for producing a corresponding spectacle lens with the spectacle power determined in this way.

BACKGROUND

A person's range of accommodation is understood as the length of the visual range of distances from the eye over which one eye of the person can see clearly. With increasing age, the range of accommodation decreases because the eye loses its accommodative power, that is to say the lens of the eye can only focus over an increasingly smaller range. The range of accommodation is given by the difference in distance between the near point and the far point. In this context, the near point of an eye is the point closest to the eye that the eye can just focus on. Accordingly, the far point is the farthest point that the eye can still focus on. The terms near point, far point and range of accommodation are defined in DIN 5340 1998-04. This standard also defines the near-point distance of an eye as the distance of the near point from the object-side cardinal point of the eye. In the context of the present application, the distance from the near point to the eyes is generally referred to as near-point distance. This near-point distance represents an approximation for the standard near-point distance. In principle, the near point can be different for the two eyes of a person. In some variants within the scope of the present application, an approximate value for the two eyes is also used as the near-point distance, for example a distance from the near point to a midpoint between the pupils of the eyes when looking straight ahead.

While the near point is around 7 cm from the eye in children, that is to say the near-point distance is around 7 cm, the near point moves further and further away from the eyes with increasing age, and so the near-point distance increases and can reach values of over 40 cm with increasing age, with the result that closer objects can no longer be seen clearly. This phenomenon is known as age-related farsightedness (presbyopia) and is independent of other refractive errors of the eyes. This presbyopia is usually corrected with reading or near-vision spectacles. If other refractive errors are present at the same time, varifocal spectacles with a distance portion for distance vision and a near portion for correcting this presbyopia may also be used.

An examination is usually carried out by an optician or ophthalmologist in order to determine the spherical power pursuant to DIN EN ISO 13666:2013 11.2 (here for reading or near-vision spectacles or for the near portion of varifocal spectacles) required for the manufacture of lenses for such spectacles, the spherical power usually being given in diopters (see DIN EN ISO 13666:2013 9.1).

This presbyopia, caused by the decreasing ability to accommodate with increasing age, typically follows a well-known curve, as described in H. Hofstetter, "Useful age-amplitude formula," Optometry and Vision Science 24(4): p. 202, April 1947, or A. Duane, Normal values of the accommodation at all ages, J. Am. Med. Assoc. 59, 1010-1013, 1912. Relatively large deviations from this curve may also allow inference of more serious health conditions, such as diabetes (see Braun C I, Benson W E, Remaley N A, Chew E Y, and Ferris Fl, "Accommodative amplitudes in the Early Treatment Diabetic Retinopathy Study," Retina, 15(4): 275-81, 1995 or side-effects of medicaments (see B. Gilmartin, "The Marton Lecture: Ocular Manifestations Of Systemic Medication," Ophthalmic and Physiological Optics, 7(4): 449-459, 1987).

Various objective and subjective measurement methods are known for measuring the range of accommodation and in particular the near-point distance. In an objective measurement method, the range of accommodation is determined without feedback from the person to be examined, while there is feedback from a person in subjective measurement methods, for example feedback as to whether a specific object is seen in focus. The present application relates to subjective measurement methods.

Conventional clinical methods for the subjective determination of the range of accommodation, in particular the near-point distance, are so-called "minus-to-blur" methods, as described in C. Sheard, "Dynamic Skiametry and Methods of Testing the Accommodation and Convergence of the Eyes," in Physiological optics, page 108, Cleveland Press, Chicago, 1920, and so-called "push-up-pull-down" methods as described in F. Donders and W. Moore, "On the anomalies of accommodation and refraction of the eye with a preliminary essay on physiological dioptrics," The New Sydenham Society, London, 1864.

In the latter method, what is known as an R.A.F. scale ("Royal Air Force Rule") is placed on the face of a person to be examined. An eye chart with optotypes, such as a script, is mounted on this scale. A treating person (e.g., a physician or optician) slowly moves this eye chart toward or away from the patient until the patient reports that they can no longer see the optotypes on the eye chart or that these can be seen in focus again. The distance of the eye chart to the patient, more specifically to the eye of the patient or to the eyes of the patient, is then read on the R.A.F. rule to give the near-point distance. This examination can be performed both monocularly, that is to say with one eye, and binocularly, that is to say with both eyes. An explanation of this measurement method is also available in the online tutorial by N. Naja retrievable from the internet at www.youtube.com/watch?v=JjrRtH0qk_0.

This conventional "push-up-pull-down" method has some disadvantages. In particular, a relatively inconvenient scale must be held in the face of the patient, the method cannot be performed alone but requires an examiner, and the scale is a rather bulky device. Efforts are therefore being made to improve and/or automate this conventional method.

Thus, Ide, Takeshi et al., "The Effect of 3D Visual Simulator on Children's Visual Acuity—A Pilot Study Comparing Two Different Modalities," The Open Ophthalmology Journal 7 (2013): 69-48, PMC, Web, Apr. 11, 2013, presents an apparatus in which a fixation target is moved driven by motor toward the person to be examined in order to determine the range of accommodation of the person. In this context, a fixation target is a component on which the person to be examined should direct their gaze. Such a fixation target can contain the aforementioned optotypes, in particular. This apparatus already allows a certain amount of automation on account of the motorized movement of the fixation target, but it is still unwieldy and is typically used at opticians or physicians.

Ide, Takeshi; Negishi, Kazuno; Yamaguchi, Takefumi; Hara, Shuya; Toda, Ikuko; and Tsubota, Kazuo, (2012), "New Compact Accommodometer to Measure Accommodation Amplitude as a Biomarker," The Asia-Pacific Journal of Ophthalmology, 1, 24-27, 1097/APO.0b013e31823f1a69, describe an apparatus which has a paper eye chart, an ultrasonic distance sensor, and corresponding readout electronics. This device can be held in the hand of a person and allows the near-point distance of the person to be determined by the person themselves, without the need for the presence of a physician or optician. However, a special device is still required in this case.

In Alec Kingsnorth, "Technological enhancements to optometric clinical tests," dissertation, Aston University, March 2015, a device is described for determining the near-point distance, the device using a smartphone as a display unit for optotypes. A distance measurement to the head of the person to be examined is carried out using ultrasonic sensors. The ultrasonic sensors required to this end and a corresponding microcontroller are housed in a case for the smartphone. An additional component to the smartphone is therefore required in this case.

US 2016/0120402 A1 discloses a method for ascertaining a refraction of the eye using a smartphone, in which the far point of the eye is determined. In the process, the distance between the eye and the smartphone is determined using a camera and a comparison with an object of known size, such as a credit card. The possibility of using an acceleration sensor to determine distance is also mentioned. This requires a calibrated initial distance, such as a zero distance directly at the eye or some other specified spacing from the eye, in order then to determine the distance by integrating the acceleration. Either an additional aid, specifically the object of known dimensions, or a fixed reference point is required in this case.

Methods for subjectively determining refraction by means of eccentric photorefraction are known from WO 2018/002332 A2, in which different options for measuring the distance between a smartphone and the head of a person are likewise used. Either these require aids, such as the aforementioned object of known dimensions and input by a user, or they use an autofocus of a smartphone camera, which may be inaccurate depending on the lighting conditions.

US 2018/116499A1 discloses a method for determining the near-point distance, in which image sensors are used to measure a distance between a mobile terminal and the eyes of a person. The person can indicate to the mobile terminal that the near point has been reached, for example by means of an acceleration sensor of the mobile terminal.

SUMMARY

It is therefore an object to provide options for determining the near point and, further, the near-point distance and the spherical power using mobile terminals such as smartphones, in which no additional aids, such as objects of known size, and also no predetermined starting point are necessary, and a sufficiently high accuracy can be achieved when determining the distance.

Further, options for determining a spherical power for a spectacle lens of reading or near-vision spectacles or for the near portion of varifocal spectacles using the near-point distance determined in this way, and for the manufacture of spectacle lenses are intended to be provided.

This object is achieved by a method for determining the near point with a mobile terminal at the near point on the basis of repeated recordings of the surroundings of the mobile terminal by the built-in camera, a method for determining the near-point distance on the basis of the positions and orientations of the mobile terminal and the identified positions of the eyes in the images, and a method for determining the spherical power on the basis of the near-point distance and reading distance of the person. Exemplary embodiments of determining the near point, further methods for determining the near-point distance, for determining a spherical power, and for producing a spectacle lens, and a corresponding computer program for carrying out the method on a mobile terminal are discussed below.

According to a first aspect of the invention, a computer-implemented method for determining the near point of a person is provided for a mobile terminal comprising a camera and an acceleration sensor, comprising:

determining the position of the mobile terminal at the near point.

The method is characterized in that the determination of the position of the mobile terminal at the near point is implemented on the basis of repeated recordings of the surroundings of the mobile terminal by a built-in camera of the mobile terminal and a repeated measurement of an acceleration of the mobile terminal by an acceleration sensor of the mobile terminal.

Other aspects of the invention expand on the first aspect of the invention.

In this way, it is possible to determine the position of the mobile terminal at the near point, which can then be used at least as an approximation for the position of the near point, using built-in sensors of the mobile terminal, specifically a camera and an acceleration sensor, which are present in any case in commercially available mobile terminals such as smartphones or tablet PCs. In this case, there is no need for additional equipment for the mobile terminal, such as ultrasonic sensors or an object of known size, and no need for a defined starting position either.

A mobile terminal should be understood to mean an apparatus which comprises at least a programmable processor and also a camera and an acceleration sensor, and which is designed to be carried, that is to say designed in respect of dimensions and weight so that a person is capable of carrying it along. Further components may be present, for example a display. Typical examples of such mobile terminals are smartphones or tablet PCs, which nowadays comprise a sensor screen (touchscreen), one or more cameras, acceleration sensors, and other components such as wireless interfaces for mobile radio or WLAN (Wireless LAN). The weight of such mobile terminals is typically less than 2 kg, usually less than 1 kg, and less than that still.

A position should be understood as a position in a stationary coordinate system, that is to say in a coordinate system that does not move with the movement of the mobile terminal. In contrast to US 2018/116499 A1 mentioned at the outset, a position and not just a distance is actually determined. Such a coordinate system is also referred to as a world coordinate system. A specification is possible, for example, in Cartesian coordinates or in spherical coordinates. Since in some applications a distance, that is to say a difference between two positions, is ultimately intended to be determined, the origin of the coordinate system in which the position is determined can be freely chosen in many cases. By way of example, the position of the mobile terminal at the time the method starts can be defined as the coordinate origin, but any other choice of coordinate origin is also possible.

An absolute determination of position is possible during the movement by repeatedly recording the surroundings and repeatedly measuring the acceleration. Such a procedure is also referred to as visual-inertial odometry and is explained in detail in, for example, G. Mitzi et al., "Fusion of IMU and Vision for absolute scale estimation in monocular SLAM," J. Intel. Robot Syst. 61, 2011, pages 287-299, and enables not only the determination of the position in a world coordinate system but also the determination of the orientation of the mobile terminal, which can be described as a tilt of a coordinate system connected to the mobile terminal relative to the world coordinate system. As explained further below, the orientation is used in some exemplary embodiments to determine the position of the eyes. The combination of position and orientation is also referred to as a pose; see DIN EN ISO 8373:2012, for example.

No special requirements are placed on the surroundings, all that needs to be present are identifiable points, for example edges of objects and the like. These are always present in a normal surroundings, for example a furnished room. In this case, the position can be determined in particular on the basis of a plurality of objects identified in the repeated recordings. These objects in the surroundings are in particular objects that are different from the person and are also not connected to them, for example carried by them.

The method may further comprise displaying optotypes on the mobile terminal. The person is able to assess whether the near point has been reached on the basis of these optotypes, for example if the optotypes still appear just in focus when the mobile terminal moves toward the person. A display is already present on mobile terminals such as smartphones or tablet PCs, and so available hardware can be used.

Optotypes should be understood to mean signs that the person can observe. Different types optotypes can be used, for example standardized optotypes (e.g., Landolt rings, E charts, possibly with further optotypes such as letters or numbers, for example, connected thereto), images, sinusoidal gratings with different spatial frequencies at the same or with varying contrast, numbers, letters or symbols. In this case, optotypes are typically displayed in different sizes. As already explained at the outset, the near point in that case is the point closest to the eyes or one eye at which the optotypes can be seen in focus.

The method can further comprise:
  requesting the person to move the mobile terminal to the near point of the person and
  receiving feedback from the person when the mobile terminal is at the near point of the person.

The request to the person can be made by way of output from the mobile terminal in this case. By way of example, the request can be made in writing or by means of symbols on the display of the mobile terminal, or by voice output using a speaker of the mobile terminal. Other output means of the mobile terminal, for example vibrations, can also be used. In this case, the person is typically requested to move the mobile terminal with the optotypes displayed thereon from a position as far away from the eyes as possible (for example, a position with the person's arm outstretched) toward the face until the near point is reached. In principle, however, it is also possible, for example, to move away from the face starting from a position directly by the eyes. In this way, no instruction by an appropriately trained additional person such as an optician is required, but rather the mobile terminal can provide the person with direct instructions for carrying out the method.

The feedback can be received via any input modality (also referred to as input means) of the mobile terminal. By way of example, a button on the mobile terminal can be pressed, a specific point on a sensor screen (touchscreen), which is also used to display the optotypes, of the mobile terminal can be touched, or feedback can be provided by the person's voice (for example, by saying a specific word like "now" or the like), which is received via a built-in microphone of the mobile terminal. Such built-in microphones are typically present in mobile terminals such as smartphones or tablet PCs.

In this case, the built-in camera can in particular be a camera which is arranged on the opposite side to a display of the mobile terminal used to display optotypes. This side is also referred to as the back side in the case of smartphones or tablet PCs, and the corresponding camera is referred to as the back camera. If the display is facing the examined person when the method is being carried out (e.g., because the person is of course supposed to assess the sharpness of the displayed optotypes), the back camera therefore faces away from the person and can record the surroundings without the person blocking the camera's "view" of the surroundings.

Furthermore, a computer-implemented method for determining the near point of a person using a mobile terminal is provided, in which the position of the near point is determined as explained above. Additionally, the method comprises the steps of:
  determining the position of at least one eye of the person and
  determining the near-point distance on the basis of the position of the mobile terminal at the near point and the position of the at least one eye.

In this way, the near-point distance can be determined using the existing hardware of mobile terminals such as smartphones or tablet PCs.

The position of the at least one eye in this case specifies the location of one eye or both eyes of the person. It is also simply referred to below as the position of the eyes of the person, it being understood that this may also relate to a position of one eye only. As will be explained below, this may also be an approximate position. The position can be determined separately for both eyes of the person. By way of example, the position of the pupils or a midpoint between the inner and outer corner of the eye can be used as the position of each eye in this case. In other exemplary embodiments, which will be explained in more detail below, the position of both eyes can also be determined as an approximate position on the basis of a position of the mobile terminal held directly against the head.

The near-point distance can then be determined as the difference between the position of the mobile terminal at the near point and a point that represents the position of the at least one eye, and as explained above this is an approximate value for the near-point distance pursuant to DIN 5340 1998-04. If the positions of both eyes are determined separately, this point, which then represents the position of both eyes, can be a midpoint of a line segment connecting the positions of the two eyes. In principle, however, it is also possible to determine the near-point distance separately for both eyes or for one eye only, by virtue of one eye always being covered and the near point being determined for the respective eye that is not covered. In this case, the near-point distance for the respective eye is a difference between the position of the eye and the position of the mobile terminal.

In the case of methods in which the position of the eyes is determined as the position of the pupils of the eyes, the interpupillary distance pursuant to DIN 33402-2, table 69 can optionally also be calculated as the distance between the pupils. This interpupillary distance (abbreviated PD) is required when fitting glasses. In this case, it can be determined without much effort in the process, with the result that a later determination is no longer necessary.

In a first variant for determining the position of the eyes, not only the position of the mobile terminal but also the orientation of the mobile terminal, that is to say the overall pose of the mobile terminal, is determined using visual-inertial odometry while the mobile terminal is moving to the near point. Moreover, an image of the eyes of the person is repeatedly recorded during the movement. The position of the eyes is then determined on the basis of the poses of the mobile terminal during the movement and the images of the eyes during the movement.

To this end, the eyes, for example the pupils thereof, are identified in the images by means of image processing and the position of the eyes is then determined in a manner similar to triangulation. A suitable image processing method for determining the position of the eyes is described in, for example, F. Timm and E. Barth, "Accurate eye center localization by means of gradients," Proceedings of the Int. Conference on Computer Theory and Applications (VISAPP), vol. 1, pages 125-130, Algarve, Portugal, 2011. Such a determination of the position of the eyes requires the poses of the mobile terminal and the corresponding images of the eyes at at least two points of the movement of the mobile terminal. As explained in the Wikipedia article "Triangulation (Messtechnik)" [Triangulation (measuring technology)] (as of Feb. 4, 2019), triangulation is a geometric method of optical distance measurement. Based on at what angles the eyes are seen at the respective poses in the image, the position of the eyes can then be determined. This approach to determining the position of the eyes will be explained in detail below in the description of the drawings.

In this way, the position of the eyes can be determined while the mobile terminal moves to the near point, and so there is no need for another separate measurement to determine the position of the eyes.

In this context, the images of the eyes of the person can be recorded in particular using what is known as a front camera, that is to say a camera arranged on the same side of the mobile terminal as the display on which the optotypes are displayed. If the person gazes at the optotypes or at the display of the mobile terminal in any other way during the intended use thereof, for example, then the eyes are in the field of view of such a front camera. Most currently available smartphones and tablets have such a front camera, and so no special hardware is required to this end.

Even if, in principle, images of the eyes in two poses of the mobile terminal are sufficient to determine the position of the eyes, the images of the eyes are preferably recorded in more than two poses in order to then be able to increase the measurement accuracy through averaging.

In an alternative approach, the determination of the position of the eyes of the person comprises the following steps:

determining, by means of visual-inertial odometry, the position of the mobile terminal at the eyes on the basis of repeated recordings of the surroundings of the mobile terminal by the built-in camera of the mobile terminal and a repeated measurement of the acceleration of the mobile terminal by the built-in acceleration sensor during the movement of the mobile terminal to the eyes, and determining the position of the eyes on the basis of the position of the mobile terminal at the eyes.

In this case, the position of the eyes is therefore determined using visual-inertial odometry, in the same way as explained above for the position of the near point.

In this context, the method may comprise requesting the person to move the mobile terminal to the eyes of the person and receiving feedback when the mobile terminal is at the eyes of the person, in order to provide the person with instructions in a manner similar to the determination of the position of the near point.

Here, the position of the mobile terminal at the eyes can be used directly as the position of the eyes. However, a certain offset, for example 1 cm or 0.5 cm, in the direction of the eyes can still be added to the position of the terminal in order to take account of the fact that, due to the person's nose, for example, a certain residual distance will always remain between the mobile terminal and the eyes. This offset can likewise be taken into account when determining the near-point distance. In this case, the position of the eyes is determined as a certain mean value in any case, specifically as the position of the mobile terminal or on the basis thereof, and no distinction is made between the two eyes.

No front camera is required for this type of determination. However, it is important in this case that the person does not, as far as possible, change the position of the head between the determination of the position of the near point and the determination of the position of the eyes.

As explained above, the determination of the near-point distance can be repeated a number of times in order to improve the accuracy by averaging over a plurality of measurements. In the process, the person may also be instructed to once move the mobile terminal toward the eyes from relatively far away until the near point is reached and to once move the said mobile terminal away from the eyes from a position immediately at the eyes until the near point is reached.

If the method is carried out occasionally by the person after relatively long periods of time, it is also possible to check whether the near-point distance follows an expected curve in order to be able to detect illnesses, as explained at the outset, where applicable.

Furthermore, a method for determining a spherical power for a spectacle lens is provided, in which the near-point distance of a person is determined using one of the methods explained above. The lens strength is then determined on the basis of the near-point distance and a reading distance.

The spherical power (abbreviated as sphere) is to be understood as defined in DIN EN ISO 13666: 2013.11.2 for near-vision spectacles or reading spectacles or as a corresponding spherical power for a near portion of varifocal spectacles.

The reading distance is understood to mean a distance from the eyes at which an object to be read is usually held by the person. The term "reading" is to be understood broadly and may also include viewing images and the like. An object to be read can be a book, for example, but can also be a mobile terminal such as a smartphone or a tablet PC, on which texts are often read nowadays (for example, e-mails or texts on websites).

In one variant, the reading distance is fixed, for example set to a range between 20 cm and 40 cm, for example 30 cm. This is advantageous in that no special measures have to be taken to determine the reading distance, but it is accompanied by a certain amount of inaccuracy, since this reading distance is assumed for all persons and not determined on an individual basis.

In a further exemplary embodiment, the user is requested to input the reading distance and the reading distance input in this way is used. A greater degree of customization is possible here, but the person has to estimate their reading distance themselves in this case.

In a further exemplary embodiment, the method comprises a determination of the reading distance with the following steps:
 determining the position of the mobile terminal in the reading position on the basis of repeatedly recording the surroundings of the mobile terminal using the built-in camera of the mobile terminal and repeatedly measuring the acceleration of the mobile terminal using the built-in acceleration sensor during a movement of the mobile terminal centrally into the reading position, and
 determining the reading distance on the basis of the position of the mobile terminal in the reading position and the position of the eyes.

Instructions can again be given to the person for this purpose. To this end, the method may comprise:
 requesting the person to bring the mobile terminal into a reading position,
 receiving feedback when the mobile terminal is in the reading position.

In this case, the position of the eyes can also be redetermined or updated, as explained above, by means of recordings of images of the eyes during the movement in order to reduce errors caused by a change in the position of the eyes.

The reading distance is then obtained as the difference between the position of the eyes and the position of the mobile terminal at the reading distance, with the explanations given above applying to the position of the eyes.

In this way, the reading distance can thus be determined on an individual basis. The use of the mobile terminal to this end is also advantageous in that specifically a reading distance is determined for mobile terminals, which are nowadays viewed more frequently than conventional reading objects such as books.

In this case, the method is carried out by the user with correctly corrected visual defects, that is to say a person who has no visual defects apart from the presbyopia explained above or whose other visual defects have already been corrected—for example by suitable spectacles. The spherical power is then calculated according to $R_{read} = (1/a_{read}) - (1/a_p) + R_{correct}$, where $R_{read}$ is the required spherical power of the reading spectacles (in diopters), $a_{read}$ is the reading distance, $a_p$ is the near-point distance and $R_{correct}$ is an optical power (in diopters) to correct residual visual defects, that is to say the optical power of a spectacle lens that the person would need without the aforementioned presbyopia. For users without any other visual defects, that is to say persons who do not otherwise wear glasses, $R_{correct}=0$. The reciprocal of the near-point distance $1/a_p$ is also called near-point refraction $A_p$.

Furthermore, a method is also provided for producing a spectacle lens, in which the spherical power is ascertained as explained above and a corresponding spectacle lens is then produced. To this end, the ascertained spherical power can be transmitted from the mobile terminal to a spectacle lens manufacturer, for example via interfaces for wireless communication that are present in the mobile terminal.

In addition, a computer program is provided, comprising commands which, when the program is executed by a mobile terminal, cause the latter to carry out one of the above-described methods for determining the near-point distance or the lens strength. Such computer programs for mobile terminals are often referred to as "apps." A corresponding computer-readable storage medium with such a computer program and corresponding data carrier signal are likewise provided.

Finally, a mobile terminal is provided, comprising:
 a display,
 a camera,
 an acceleration sensor, and
 a processor configured so that it causes one of the above-described methods for determining the near point, the near-point distance or the spherical power to be carried out on the mobile terminal, that is to say so that at least the following steps are carried out:
 determining the position of the mobile terminal at the near point,
 the determination of the position of the mobile terminal at the near point being implemented on the basis of repeated recordings of the surroundings of the mobile terminal by a built-in camera of the mobile terminal and on the basis of a repeated measurement of an acceleration of the mobile terminal by a built-in acceleration sensor of the mobile terminal during a movement of the mobile terminal to the near point.

To this end, a corresponding computer program can be provided in a memory of the mobile terminal, or the mobile terminal can comprise corresponding means that carry out the method steps.

In this way, the near-point distance can be determined using a mobile terminal and then the lens strength can be determined in developments.

BRIEF DESCRIPTION OF THE DRAWINGS

The disclosure will now be described with reference to the drawings wherein.

DESCRIPTION OF EXEMPLARY EMBODIMENTS

Figure 1:
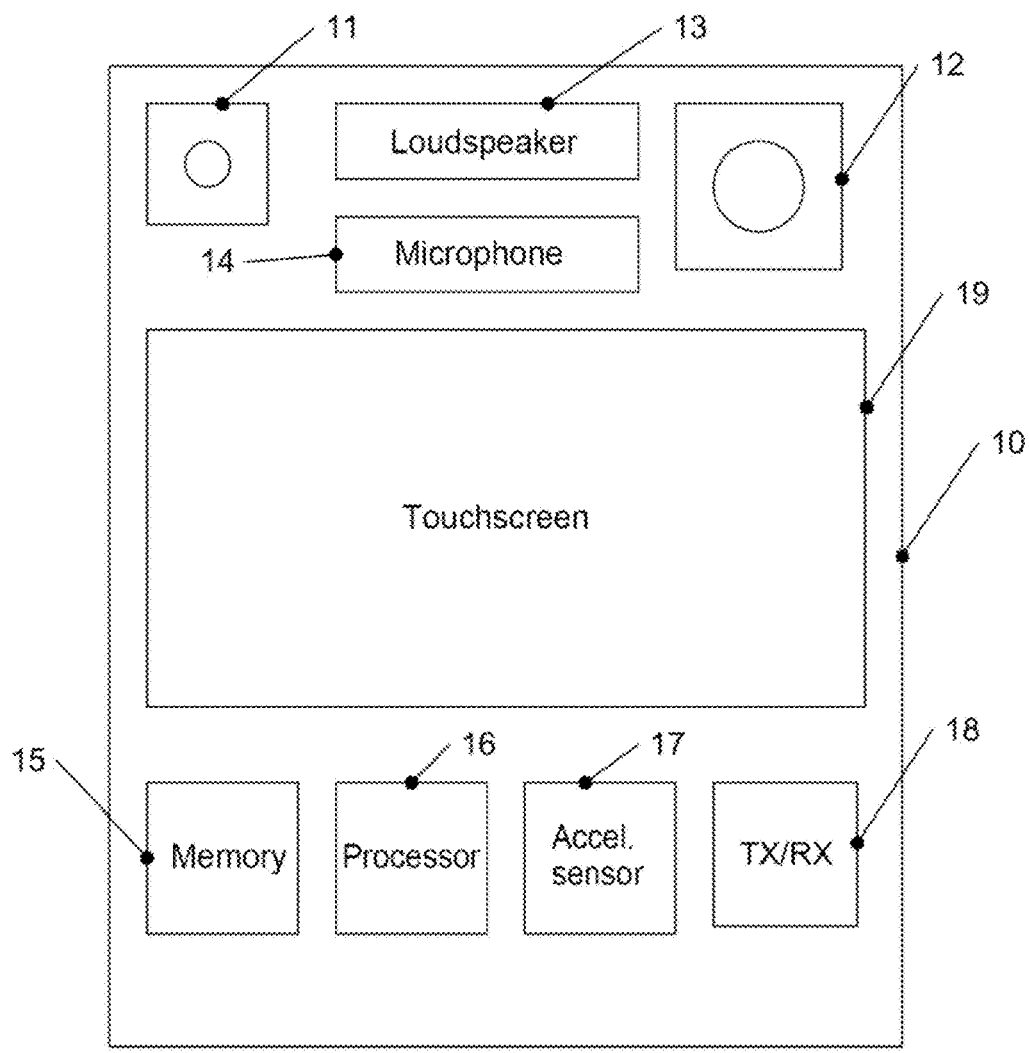
FIG. 1 shows a block diagram of a mobile terminal such as is used in various exemplary embodiments.

The exemplary embodiments described below use a mobile terminal to determine the near-point distance of a person and further to determine a spherical power, on the basis of which spectacle lenses can then be manufactured. FIG. 1 shows a block diagram of a mobile terminal such as is used in such exemplary embodiments. In this case, the mobile terminal can be a smartphone or a tablet computer, which typically contain at least the components shown in FIG. 1.

The mobile terminal 10 in FIG. 1 has a sensor screen 19 (referred to as "touchscreen"), which serves as an input device and also for outputting and for displaying optotypes when methods according to the invention are carried out. The mobile terminal 10 is controlled by a processor 16, which can access a memory 15, in which computer programs can be stored. As a ready mentioned, such computer programs for mobile terminals are also referred to as apps. The mobile terminal 10 furthermore has a loudspeaker 13 for outputting sounds, and a microphone 14, by means of which it is possible to receive voice commands, for example. The mobile terminal 10 furthermore comprises a front camera 11 and a back camera 12. In this case, the front camera 11 is arranged on the same side as the touchscreen 19, such that a person, in particular the eyes of a person observing the touchscreen 19, can be captured by means of the camera 11. The back camera 12 is arranged on the opposite side of the mobile terminal 10 to the touchscreen 19.

Furthermore, the mobile terminal 10 comprises an acceleration sensor 17 with which accelerations of the mobile terminal 10 can be measured. Finally, provision is made for a communication circuit 18 for transmitting (TX, from transmit) and receiving (RX, from receive) data, for example via a mobile radio network and/or via a WLAN network (Wireless LAN).

Figure 2:
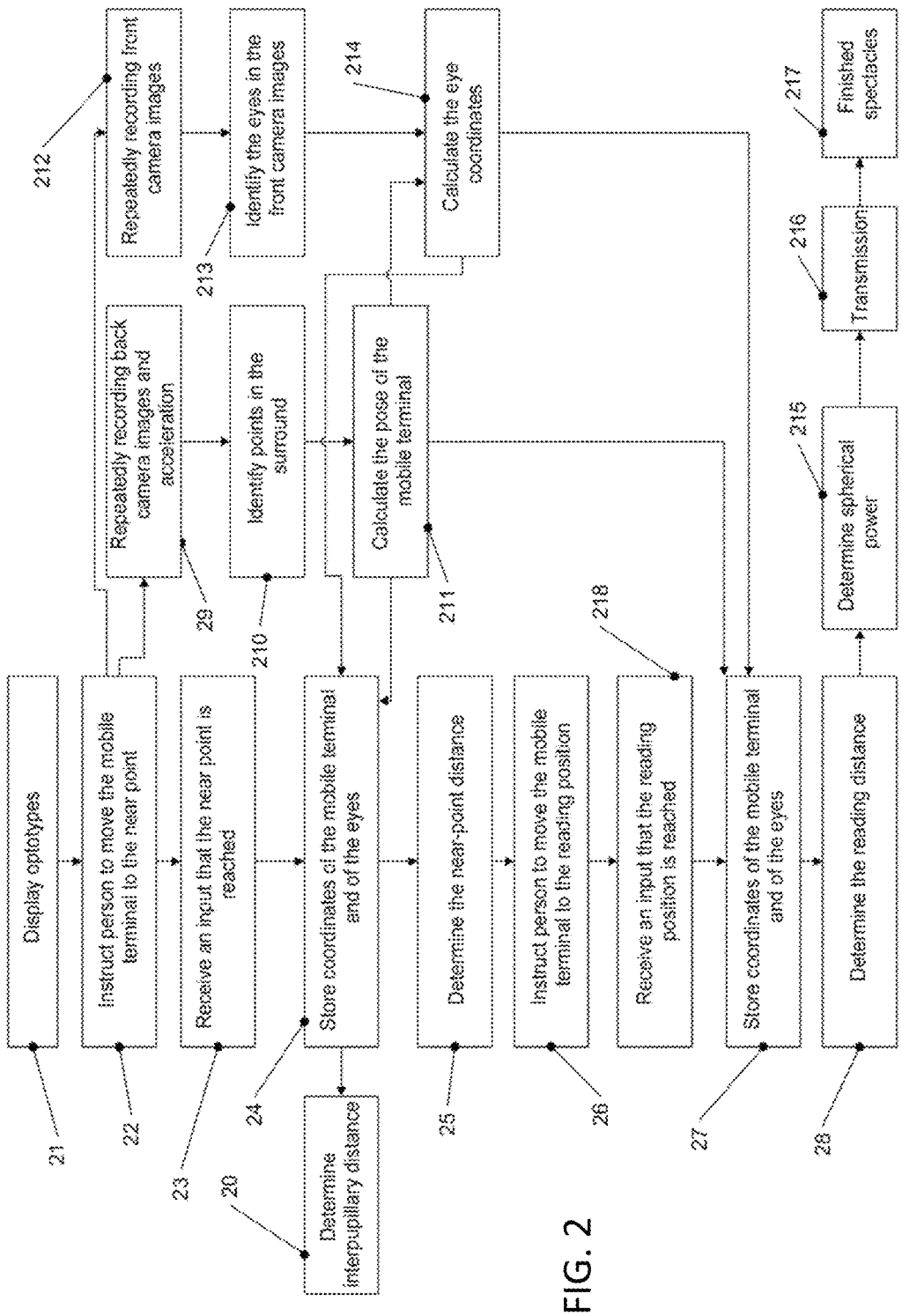
FIG. 2 shows a flowchart of a method according to one exemplary embodiment.

FIG. 2 shows a flowchart of a method according to one exemplary embodiment. The method in FIG. 2 can be carried out using the mobile terminal 10 of FIG. 1 and will be described with reference to the mobile terminal 10 of FIG. 1. For additional explanation of the method in FIG. 2, reference is made to FIGS. 3A, 3B and 4.

In step 21, optotypes are displayed on the touchscreen 19 of the mobile terminal 10. In step 22, a person to be examined is instructed to move the mobile terminal to the near point. This instruction in step 22 can be given via a display on the touchscreen 19 or by voice output from the loudspeaker 13.

Figure 3A:
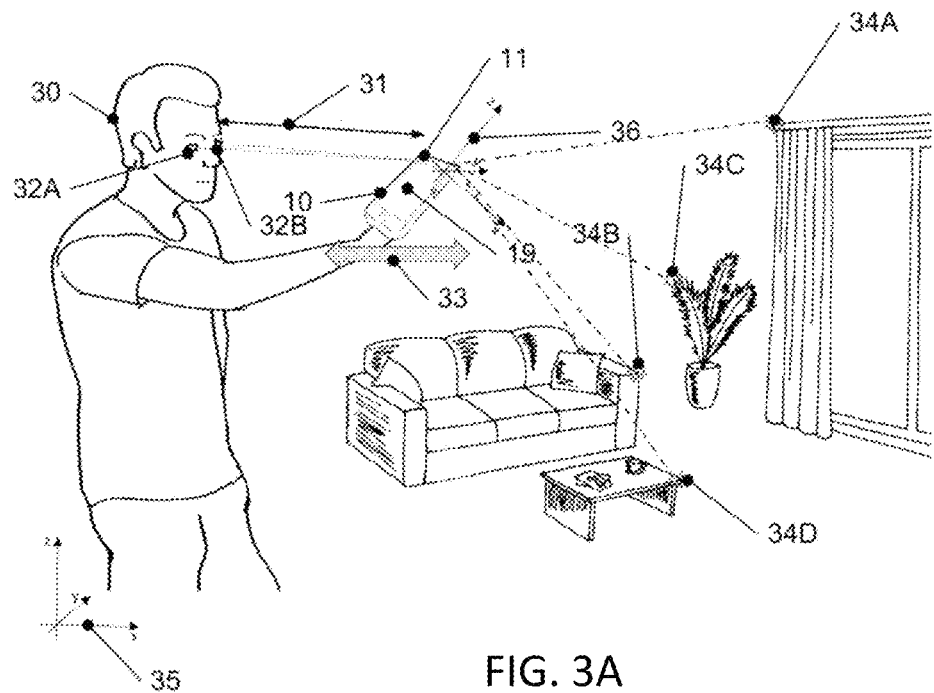
FIGS. 3A and 3B show diagrams to illustrate different method steps of FIG. 2.

This movement to the near point is depicted schematically in FIG. 3A. Here, a person 30 holds the mobile terminal 10 in such a way that they can gaze at the touchscreen 19. After the instruction in step 22, the person 30 moves the mobile terminal 10 from a relatively large distance toward the eye, for example as indicated by an arrow 33, until they can just see the optotypes on the touchscreen 19 in focus. Alternatively or else additionally when carrying out the method repeatedly, the person can first hold the mobile terminal 10 close to eyes 32A, 32B (hereinafter referred to collectively as eyes 32) and then move the mobile terminal 10 away from the eyes until the optotypes can be seen in focus. At the end of this movement, the mobile terminal 10 is at the near point and in step 23 in FIG. 2 the mobile terminal receives input from the person 30 confirming that the near point has been reached. This input can take place via the touchscreen 19 or via the loudspeaker 13.

During this movement according to arrow 33 in FIG. 3, images are repeatedly recorded using the back camera 12 of the mobile terminal and acceleration data are recorded using the acceleration sensor 17 in step 29. The rate at which this repetition takes place is substantially limited by the computing power of the mobile terminal, that is to say by how quickly the recorded images and measured accelerations can be recorded and processed. In this context, higher rates can lead to a greater accuracy. In step 210, corresponding points, so-called feature points, are identified in the recorded images of the surroundings. In this context, corresponding points are points that show the same part of the same object in each image. Various such points 34A through 34D are shown in FIG. 3A for purposes of illustration. As can be seen, these points can be corners of pieces of furniture (points 34B, 34D), points on a plant (point 34C), or points on features of rooms such as a curtain rail (point 34A). Points that have a clear structure in their local environment in terms of color and/or brightness differences are usually used in this case. These are relatively easily identifiable using conventional image processing methods. E. Salahat and M. Qasaimeh, "Recent advances in features extraction and description algorithms: A comprehensive survey," 2017 *IEEE International Conference on Industrial Technology (ICIT)*, Toronto, ON, 2017, pages 1059-1063, provide an overview of various methods that can be used in this respect.

In step 211, the pose of the mobile terminal 10, that is to say the position and orientation of the mobile terminal, is continuously determined by means of visual-inertial odometry from the acceleration data and the recorded images with the points identified therein. When the user input is received in step 23, the position of the mobile terminal at that time corresponds to the position of the near point.

The position of the mobile terminal is calculated in a world coordinate system 35 of FIG. 3A in the process. As already explained, the origin of this world coordinate system can be chosen freely. The orientation can be specified as a tilt of a coordinate system 36 connected to the mobile terminal in relation to the world coordinate system 35.

Moreover, images are repeatedly recorded using the front camera 19 of the mobile terminal during the movement toward the near point in step 212 and the eyes 32 of the person are visible in the said images, as is likewise indicated in FIG. 3A. In step 213, the eyes are identified in these images. In step 214, the position of the eyes is then calculated on the basis of the identification of the eyes in the front camera images and the respective pose of the mobile terminal (calculated in step 211) when recording the front camera images. The position of the eyes and the position of the mobile terminal at the near point are then stored in step 24 as coordinates in the world coordinate system 35.

The calculation of the position of the eyes of step 214 will now be explained in more detail with reference to FIG. 4.

Figure 4:
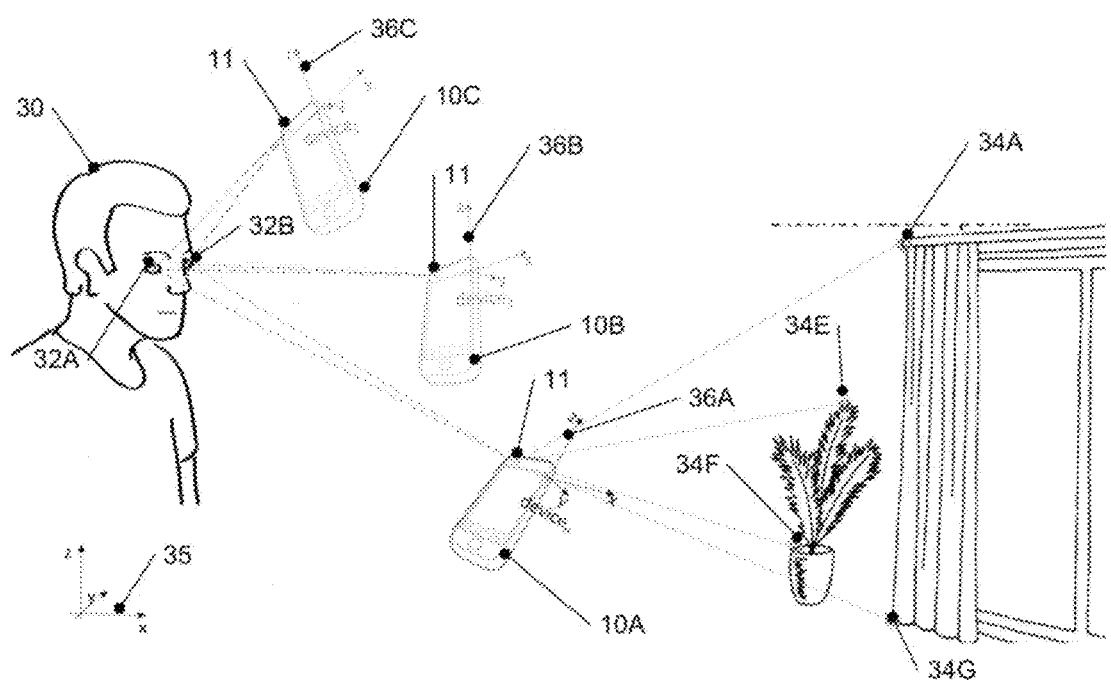
FIG. 4 shows a diagram to illustrate a determination of a position of the eyes according to some exemplary embodiments.

In FIG. 4, the mobile terminal 10 is shown in three different poses as a mobile terminal 10A, 10B, and 10C, respectively, for explanation purposes. The coordinate system 36 coupled to the mobile terminal moves with the mobile terminal 10 in this case and is shown as the coordinate system 36A, 36B, and 36C, respectively, in FIG. 4. By way of example, the mobile terminal 10 assumes such multiple poses when moving toward the near point following the instruction in step 22.

As explained with reference to FIG. 2, acceleration sensor data is recorded and the surroundings with the points is recorded using the back camera of the mobile terminal 10A (points 34A, 34E, 34F and 34G are shown in the example of FIG. 4) during the movement, with the result that, as discussed, the pose of the mobile terminal 10 can be determined by means of visual-inertial odometry at any point during the movement. As mentioned, the pose is specified as the position of the mobile terminal in the world coordinate system 35 and the orientation as a tilt of the coordinate system 36 with respect to the world coordinate system 35.

In principle, two poses are sufficient to determine the position of the eyes. However, since the movement of the mobile terminal 10 typically takes place along a comparatively straight line toward the eyes and therefore the difference between the poses transverse to this direction is relatively small in comparison with a line that points directly toward the eyes, the accuracy can be increased by a higher number of poses. Preferably, 2 to 20 different poses of the mobile terminal 10 are used to determine the position of the eyes of the person 30. The depiction of three different poses in FIG. 4 is only one example. This is because, in principle, such a determination of position similar to triangulation benefits from a greater distance transversely to a line toward the object whose position is intended to be determined (in this case the eyes), and in the present case this can be compensated for by a larger number of poses and averaging associated therewith.

The position of the eyes, for example of the pupils of the eyes or of the corners of the eyes of the person 30, is detected in the images using image processing methods. A digital image captured by a camera usually consists of a rectangular arrangement of picture elements (also referred to as pixels). The positions of the eyes can then be given as two-dimensional coordinates in this rectangular array of pixels.

The calculation now presented applies to one eye. The same calculation can be carried out for the other eye in order thus to calculate the position of both eyes. The coordinates of the eye in the image are specified in homogeneous coordinate notation as $$y_n = \begin{pmatrix} y_1 \\ y_2 \\ 1 \end{pmatrix}. \tag{1}$$

Such homogeneous coordinates are often used in projective geometry; see Wikipedia article "Homogene Koordinaten" [Homogeneous coordinates], as of Feb. 4, 2019. The index n of $y_n$ represents the number of the pose, that is to say, for example, a respective value $y_n$ is available for each pose of the mobile terminal 10A, 10B, 10C.

In the world coordinate system 35, by contrast, the eye has the position $$x_{world} = \begin{pmatrix} x_1 \\ x_2 \\ x_3 \\ 1 \end{pmatrix}, \tag{2}$$

likewise in homogeneous notation.

The relationship between $y_n$ and $x_{world}$ is given by $$y_n = C \cdot X_n \cdot x_{world} \tag{3}$$

Here, C is the so-called camera matrix, which describes the perspective projection onto a two-dimensional image sensor of the camera. C is defined for a specific camera and can be ascertained for different models of mobile terminals, for example by calibration measurements, or can be provided by the manufacturer of the mobile terminal. For a simple pinhole camera, the following applies:

$$C = \begin{pmatrix} f & 0 & 0 & 0 \\ 0 & f & 0 & 0 \\ 0 & 0 & 1 & 0 \end{pmatrix} \tag{4}$$

Here, f is the focal length of the pinhole camera. X is the transformation matrix describing the Euclidean coordinate transformation from points in the world coordinate system (35 in FIG. 4) to the respective camera coordinate system corresponding to the coordinate system 36 (36A, 36B, and 36C in FIG. 4) associated with the mobile terminal 10. X is given by $$X = \begin{pmatrix} R_n & t_n \\ 0 & 1 \end{pmatrix} \tag{5}$$

$R_n$ is the rotation matrix which describes the rotation of the coordinate system 36 with respect to the coordinate system 35 (i.e., the orientation), and $t_n$ is a translation vector which shows the respective position of the mobile terminal 10, expressed as a displacement of the coordinate origin of the coordinate system 36 to the coordinate origin of the coordinate system 35.

In this case, the position can be specified as the position of a specific point on the mobile terminal 10. The origin of the coordinate system 36 can be placed at this point of the mobile terminal.

X is therefore known from the measurement of the pose of the mobile terminal using visual-inertial odometry. $y_n$ is known from the image recordings of the eyes of the person using the front camera 19 of the mobile terminal 10. C is fixed for a respective mobile terminal and describes the camera properties. Therefore, only the coordinates $x_{world}$ of the respective eye in the world coordinate system are unknown in equation (3). From a plurality of measurements, that is to say a number of poses of the mobile terminal as shown in FIG. 4, the resultant system of equations can be solved for the eye coordinates $x_{world}$ using methods of linear algebra and/or numerical optimization. Such approaches are described in the Wikipedia article "Direct linear transformation," available online at en.wikipedia.org/wiki/Direct_linear_transformation as of Jun. 4, 2021, and the references cited there.

As already mentioned, the coordinates of the eyes ascertained in this way are stored in step 24 in FIG. 2.

If the positions of the pupils are used as the positions of the eyes, the interpupillary distance PD is optionally determined as the distance between the coordinates of the pupils of the eyes from the coordinates of the eyes in step 20.

In step 25, the near-point distance is determined as the distance between the near point and the eyes. In this case, the coordinates of the mobile terminal at the near point stored in step 24 are used as the position of the near point. In the method in FIG. 4, the center of a connecting line between the coordinates of the two eyes is used as the position of the eyes.

The near-point distance is marked by an arrow 31 in FIG. 3A.

In this way, the near-point distance can be determined using the method in FIG. 2. Further method steps, which will now be explained, serve to determine the spherical power for a pair of reading spectacles.

The next steps of the method in FIG. 2 serve to determine the reading distance. As explained at the outset, a predetermined value or a value input by the user can also be used for the reading distance instead.

In step 26, the person is instructed to move the mobile terminal to a reading position, that is to say hold it at a reading distance. Like in step 22, this instruction can be given by a display on the touchscreen 19 or else by an output from the loudspeaker 13.

In step 218, input from the person that the reading position has been reached is received by the mobile terminal. Like in step 23, this can be implemented, for example, by appropriately touching the touchscreen or by way of a voice input.

During the movement to the reading distance, steps 29 and 210 and then also step 211 continue to be carried out. In addition, steps 212, 213 and 214 can also continue to be performed in order to update the position of the eyes if the user has changed the position of the eyes since step 24 by movements. In step 27, the coordinates of the mobile terminal in the reading position and the coordinates of the eyes are then stored in a manner similar to step 24. In other exemplary embodiments, the position of the eyes, which was stored in step 24, can continue to be used. In this case, the person should, as far as possible, not change the position of their eyes between steps 24 and 27.

Figure 3B:
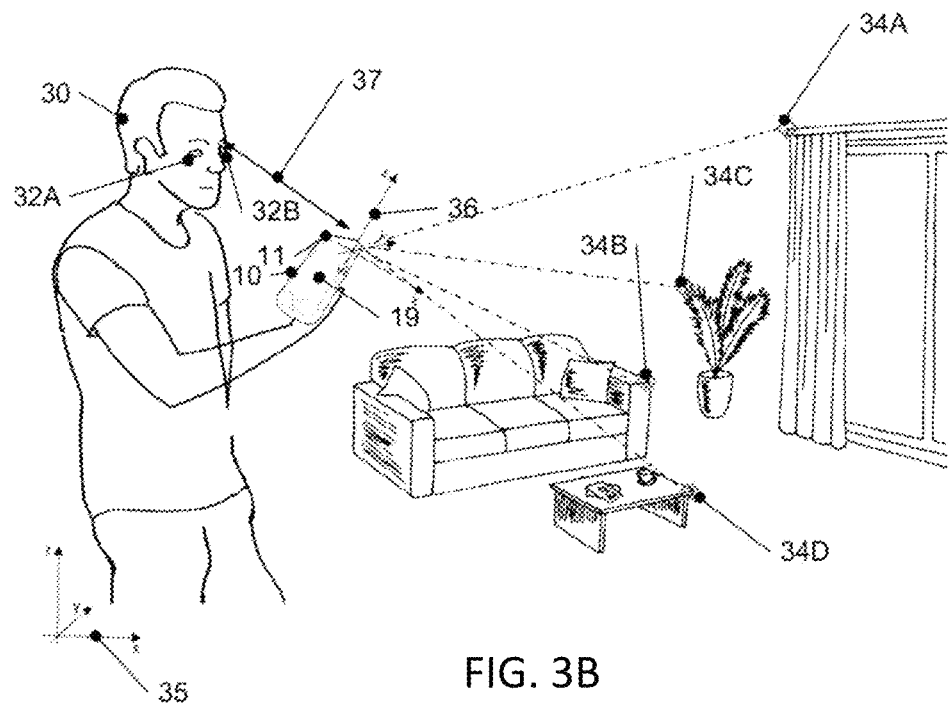

Steps 26, 218, and 27 are illustrated in FIG. 3B. In FIG. 3B, the person 30 has moved the mobile terminal 10 to the reading position, that is to say a position at which they typically gaze at the touchscreen 19 of the mobile terminal 10. The back camera continues to record the surroundings, in particular points 34A to 34D, and in this way, together with data from the acceleration sensor 17, determines the position of the mobile terminal 10 in the world coordinate system 35.

In step 28 in FIG. 2, the coordinates stored in step 27 then become the reading distance as the distance between the mobile terminal in the reading position and the eyes. The same as already explained for step 25 applies to the distance between the eyes, that is to say a midpoint of a line segment between the coordinates of the left eye and the right eye can be used as the position of the eyes for the purpose of determining the distance.

The reading distance is marked by an arrow 37 in FIG. 3B.

In step 215, the spherical power is determined from the near-point distance determined in step 25 and from the reading distance determined in step 28, as explained above.

In step 216, the spherical power is then transmitted via the communication circuit 18 of the mobile terminal to a spectacle lens manufacturer, where corresponding spectacle lenses are then manufactured in step 217.

Figure 5:
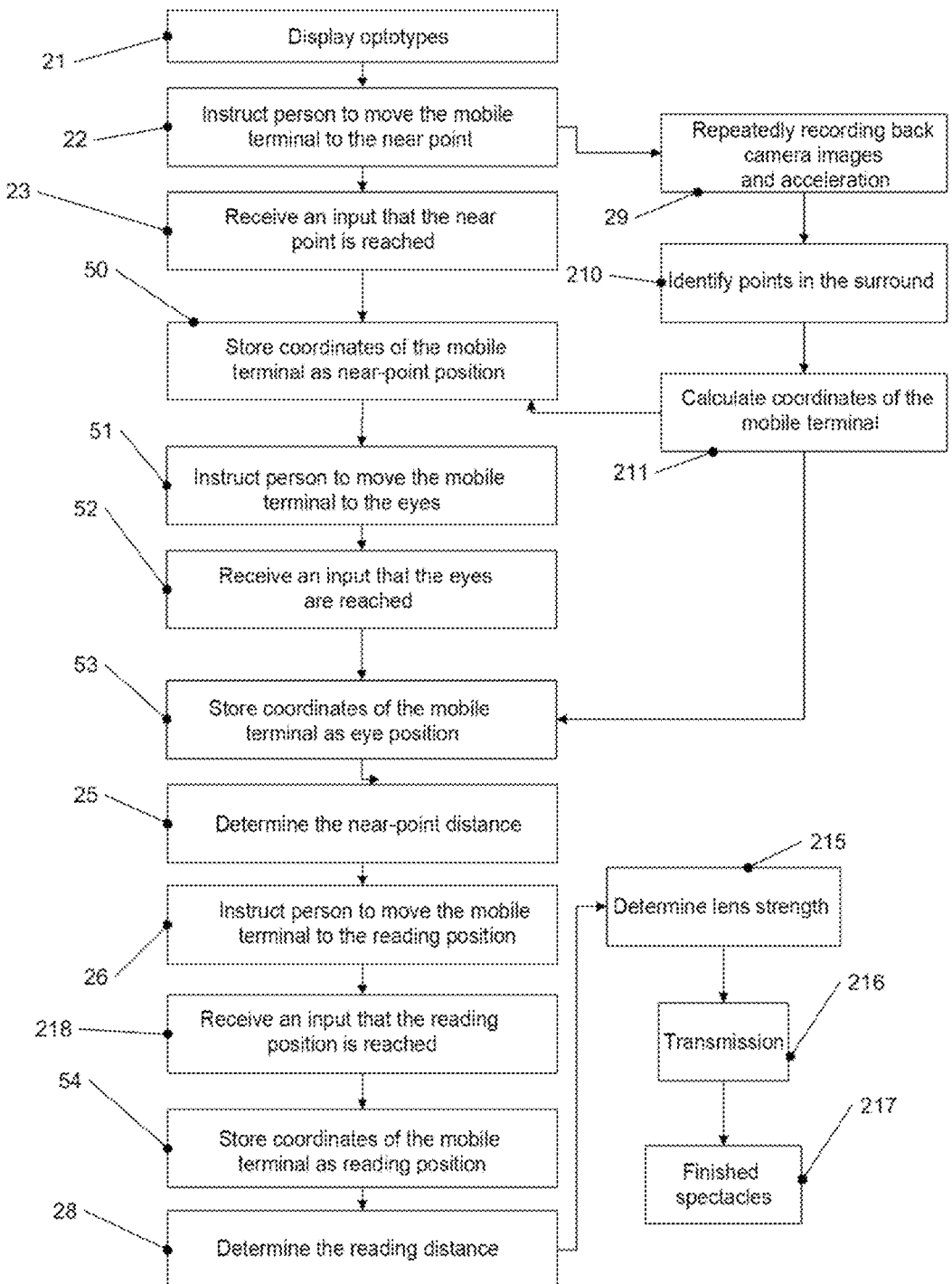
FIG. 5 shows a flowchart of a method according to a further exemplary embodiment.

A further method is illustrated in FIG. 5. To avoid repetition, reference to the description of the method in FIG. 2 is made in the description of the method in FIG. 5. Moreover, FIGS. 6A to 6C are used to illustrate the method in FIG. 5.

Steps 21 to 23 of the method in FIG. 5 correspond to steps 21 to 23 in FIG. 2, that is to say optotypes are displayed on the touchscreen 19 of the mobile terminal 10, the person is instructed to move the mobile terminal to the near point, and the mobile terminal 10 receives a user input when the near point is reached. Steps 29 to 211 are carried out in parallel therewith, like in the method in FIG. 2. In contrast to step 211 in FIG. 2, only the position of the mobile terminal has to be calculated in step 211 in FIG. 5, and not the entire pose including orientation, since the orientation is not required for the method in FIG. 5.

Then, in step 50, the coordinates of the mobile terminal in the position where the input of the person is received in step 23 are stored as the near-point position.

Figure 6A:
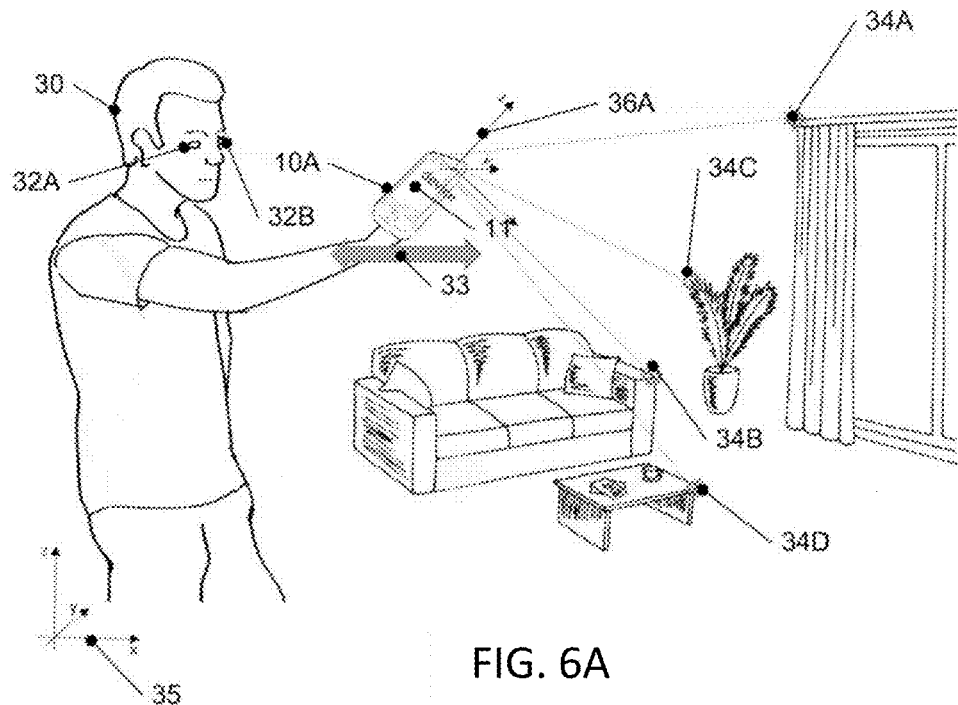
FIGS. 6A to 6C show diagrams to illustrate some method steps of FIG. 5.
Figure 6B:
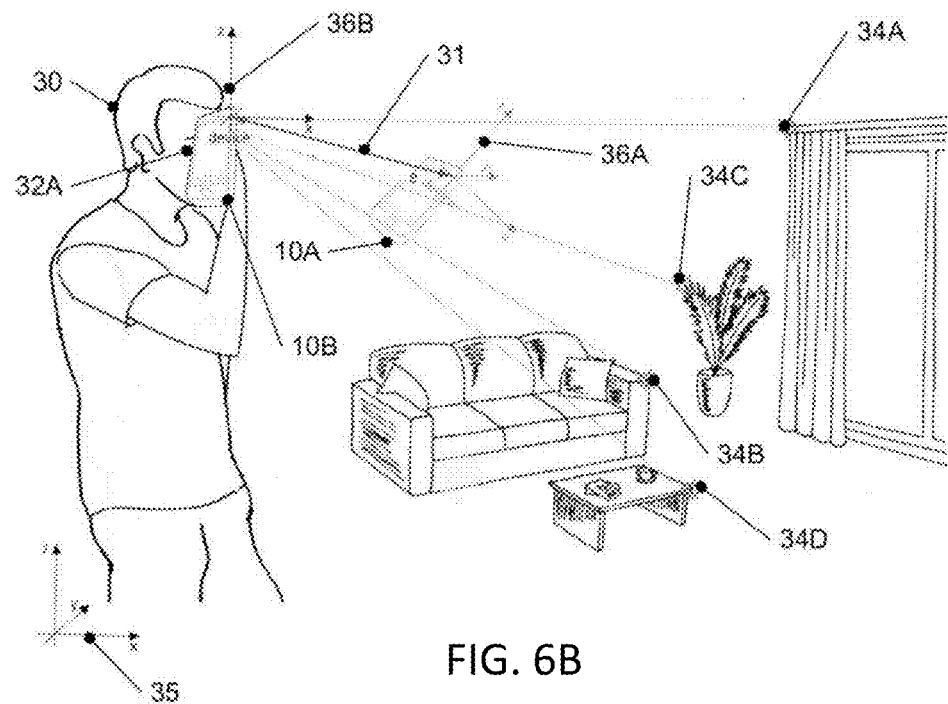
Figure 6C:
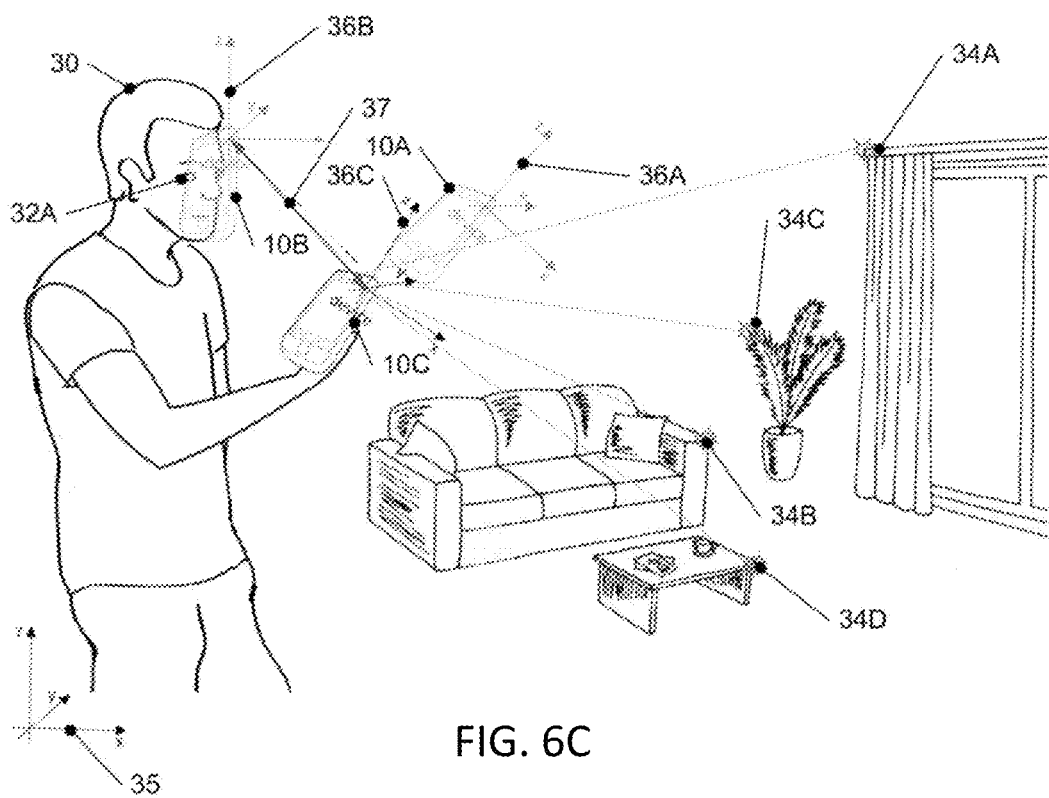

Steps 21, 22, 23, 50 and steps 29, 210, 211 executed in the process are illustrated in FIG. 6A. In this context, FIG. 6A largely corresponds to FIG. 3A, with the mobile terminal at the near point being denoted by the reference sign 10A and the associated coordinate system being denoted by the reference sign 36A in this case in order to distinguish these from positions used at a later stage during the further course of the method.

In step 51, the person is then instructed to move the mobile terminal to the eyes. Like in step 22, the instruction can be given via an output on the touchscreen or an output from the loudspeaker 13.

In step 52, a user input that the eyes are reached is received. During the movement to the eyes, steps 29, 210 and 211 are again executed and the coordinates of the position of the mobile terminal when the input is received in step 52 are stored as the eye position in step 53. Steps 51 and 52 and steps 29 to 211 executed in parallel therewith are shown in FIG. 6B. Here, the person 30 has moved the mobile terminal to the eyes. In this position, the mobile terminal is denoted by the reference sign 10B.

In step 25, the near-point distance is then determined as the distance between the coordinates stored in step 50 and the coordinates stored in step 53. In some cases, a certain offset, for example 0.5 cm or 1 cm, can be added to the near-point distance determined as the difference in coordinates in order to determine the near-point distance, in order to take account of the fact that, due to the anatomy of the face, the mobile terminal may possibly still be at a certain distance from the eyes.

Steps 26 and 218 again correspond to steps 26 and 218 in FIG. 2, that is to say the user is instructed here to move the mobile terminal to the reading position and the mobile terminal receives a user input after the reading position is reached at 218. In the meantime, steps 29 to 211 are executed again, and, in step 54, the coordinates of the mobile terminal when the user input from step 218 is received are stored as the reading position. This is illustrated in FIG. 6C, where the person 30 holds the mobile terminal 10 in the reading position, in which the mobile terminal is denoted by reference sign 10C. In step 28, the reading distance is then calculated as the difference between the coordinates stored in steps 53 and 54, with an offset being able to be added in this case, too, in order to take a distance of the mobile terminal from the eyes into account when the mobile terminal is held against the head directly in front of the eyes.

The reading distance is marked by an arrow 37 in FIG. 6C.

Steps 215 to 217 of the method in FIG. 5 once again correspond to steps 215 to 217 in FIG. 2. In comparison with FIG. 2, the method in FIG. 5 does not require the determination of the eye positions by means of triangulation; for this, the person 30 still has to move the mobile terminal into a third position, specifically into a position as close as possible to the eyes.

The methods in FIGS. 2 and 5 can be implemented in particular by a corresponding program which is stored in the memory 15 of the mobile terminal and is executed on the processor 16.

Some exemplary embodiments are defined by the following clauses:

Clause 1. A computer-implemented method for determining the near point (31) of a person (30) using a mobile terminal, comprising:
determining the position of the mobile terminal (10) at the near point,
characterized
in that the determination of the position of the mobile terminal at the near point is implemented on the basis of repeated recordings of the surroundings of the mobile terminal (10) by a built-in camera (11, 12) of the mobile terminal (10) and on the basis of a repeated measurement of an acceleration of the mobile terminal (10) by a built-in acceleration sensor (17) of the mobile terminal during a movement of the mobile terminal (10) to the near point.

Clause 2. The method according to clause 1, characterized by:

displaying optotypes on the mobile terminal (10).

Clause 3. The method according to clause 1 or 2, characterized by requesting the person (30) to move the mobile terminal (10) to the near point of the person, receiving feedback when the mobile terminal is at the near point of the person (30).

Clause 4. The method according to any one of clauses 1 to 3, characterized in that the repeated recordings are made by a back camera of the mobile terminal (10), which is arranged on the opposite side of the mobile terminal to a display (19) of the mobile terminal (10).

Clause 5. A computer-implemented method for determining the near-point distance (31) of a person (30) using a mobile terminal, characterized by:

determining the near point of the person by means of the method according to any one of clauses 1 to 4, determining the position of at least one eye (32A, 32B) of the person (30), and determining the near-point distance (31) on the basis of the position of the mobile terminal (10) at the near point and the position of the at least one eye (32A, 32B).

Clause 6. The method according to clause 5, characterized in that the determination of the position of the at least one eye comprises:

during the movement of the mobile terminal (10) to the near point of the person, repeatedly determining the position and orientation of the mobile terminal (10) on the basis of the repeated recordings of the surroundings and the repeated measurement of the acceleration, and repeatedly recording an image of the at least one eye of the person using the built-in camera (12) or a further built-in camera (11) of the mobile terminal (10), identifying the at least one eye in the images of the at least one eye of the person (30), and determining the position of the at least one eye (32A, 32B) of the person on the basis of the positions and orientations of the mobile terminal and the identified positions of the eyes in the images.

Clause 7. The method according to clause 6, wherein the position of the at least one eye comprises the positions of both eyes of the person, wherein the positions of the eyes comprise positions of the pupils of the eyes, and wherein the method further comprises a determination of the interpupillary distance on the basis of the positions of the pupils.

Clause 8. The method according to clause 6 or 7, wherein the position of the at least one eye comprises the positions of both eyes of the person and wherein the determination of the near-point distance comprises a determination of the near-point distance as the distance between the position of the mobile terminal at the near point and a midpoint of a connecting line between the positions of the eyes.

Clause 9. The method according to any one of clauses 6 to 9, wherein repeatedly recording the image of the at least one eye is implemented using a front camera (11) of the mobile terminal (10), which is arranged on the same side of the mobile terminal (10) as a screen (19) of the mobile terminal.

Clause 10. The method according to clause 5, characterized in that the determination of the position of the at least one eye of the person comprises:

determining the position of the mobile terminal at the eyes of the person on the basis of repeatedly recording the surroundings of the mobile terminal (10) using the built-in camera (11, 12) of the mobile terminal (10) and repeatedly measuring of the acceleration of the mobile terminal (10) using the built-in acceleration sensor (17) of the mobile terminal during a movement of the mobile terminal (10) to the eyes by the built-in acceleration sensor (17) of the mobile terminal of the person.

Clause 11. The method according to clause 10, characterized by:

requesting the person to move the mobile terminal to the eyes (32A, 32B) of the person (30), receiving feedback when the mobile terminal (10) is at the eyes (32A, 32B) of the person.

Clause 12. A method for determining a spherical power for a spectacle lens, comprising:

determining the near-point distance (31) of the person (30) by means of the method according to any one of clauses 5 to 11 and determining the spherical power on the basis of the near-point distance (31) and a reading distance (37) of the person.

Clause 13. The method according to clause 12, wherein the reading distance is a predetermined reading distance, or wherein the reading distance is input by the person (30).

Clause 14. The method according to clause 12, characterized in that the method further comprises:

determining the position of the mobile terminal (10) in the reading position on the basis of repeatedly recording the surroundings of the mobile terminal (10) using the built-in camera (11, 12) of the mobile terminal (10) and repeatedly measuring the acceleration of the mobile terminal (10) using the built-in acceleration sensor (17) of the mobile terminal during a movement of the mobile terminal (10) into the reading position, and determining the reading distance on the basis of the position of the mobile terminal (10) in the reading position and the position of the eyes.

Clause 15. The method according to clause 14, characterized by:

requesting the person to move the mobile terminal (10) into a reading position of the person (30), receiving feedback when the mobile terminal (10) is in the reading position.

Clause 16. A method for producing a spectacle lens, comprising:

determining the spherical power, according to any one of clauses 12 to 15, producing a spectacle lens on the basis of the determined spherical power.

Clause 17. A computer program for a mobile terminal comprising a camera (11, 12) and an acceleration sensor (17), comprising instructions which, when the computer program is executed by a mobile terminal (10), cause the latter to carry out the method according to any one of clauses 1 to 15.

Clause 18. A computer-readable non-volatile data medium, on which the computer program according to clause 17 is stored.

Clause 19. A data medium signal, which transmits the computer program according to clause 17.

Clause 20. A mobile terminal, comprising:
a built-in camera (11, 12),
an acceleration sensor (17), and
a processor (16) configured so that the following steps are carried out:
determining the position of the mobile terminal (10) at the near point,
characterized
in that the determination of the position of the mobile terminal at the near point is implemented on the basis of repeated recordings of the surroundings of the mobile terminal (10) by a built-in camera (11, 12) of the mobile terminal (10) and on the basis of a repeated measurement of an acceleration of the mobile terminal (10) by a built-in acceleration sensor (17) of the mobile terminal during a movement of the mobile terminal (10) to the near point.

Clause 21. The mobile terminal according to clause 20, characterized in that the processor is configured so that the method according to any one of clauses 1 to 15 is carried out.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of" The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A method for a mobile terminal having a built-in camera, a built-in acceleration sensor, and a processor, for determining a near point of a person, the method comprising:
performing a movement of the mobile terminal in front of the person;
repeatedly recording surroundings of the mobile terminal by the built-in camera of the mobile terminal,
the repeated recordings including at least one object other than the person;
repeatedly measuring an acceleration of the mobile terminal by the built-in acceleration sensor of the mobile terminal during a movement of the mobile terminal to the near point of the person; and
determining a position of the mobile terminal at the near point of the person based on the repeated recordings and the repeated measurements.

2. The method as claimed in claim 1, wherein the determination of the position of the mobile terminal at the near point is implemented by the processor by visual-inertial odometry.

3. The method as claimed in claim 1, wherein the determination of the position of the mobile terminal at the near point is implemented by the processor based on a plurality of objects identified in the repeated recordings of the surroundings of the mobile terminal.

4. The method as claimed in claim 1, wherein the determination of the position of the mobile terminal at the near point is implemented by the processor as a determination of position in a stationary coordinate system.

5. The method as claimed in claim 1, wherein the repeated recordings are made by a back camera of the mobile terminal, which is arranged on an opposite side of the mobile terminal to a display of the mobile terminal.

6. The method as claimed in claim 1, further comprising:
requesting the person to move the mobile terminal to the near point of the person by using output means of the mobile terminal; and
receiving feedback when the mobile terminal is at the near point of the person by using input means of the mobile terminal.

7. A method for a mobile terminal having a built-in camera, a built-in acceleration sensor, and a processor, for determining a near-point distance of a person, the method comprising:
determining the near point of the person with the method as claimed in claim 1;
determining the position of at least one eye of the person; and
determining the near-point distance based on the position of the mobile terminal at the near point and the position of the at least one eye.

8. The method as claimed in claim 7, wherein the determination of the position of the at least one eye comprises:
during the movement of the mobile terminal to the near point of the person, repeatedly determining the position and orientation of the mobile terminal based on the repeated recordings of the surroundings and the repeated measurement of the acceleration, and repeatedly recording an image of the at least one eye of the person using the built-in camera or a further built-in camera of the mobile terminal;
identifying the at least one eye in the images of the at least one eye of the person; and
determining the position of the at least one eye of the person based on the positions and orientations of the mobile terminal and the identified positions of the eyes in the images.

9. The method as claimed in claim 8, wherein the position of the at least one eye includes the positions of both eyes of the person and wherein the determination of the near-point distance includes a determination of the near-point distance as the distance between the position of the mobile terminal at the near point and a midpoint of a connecting line between the positions of the eyes.

10. The method as claimed in claim 8, wherein repeatedly recording the image of the at least one eye is implemented using a front camera of the mobile terminal, which is arranged on a same side of the mobile terminal as a screen of the mobile terminal.

11. The method as claimed in claim 7, wherein the determination of the position of the at least one eye of the person comprises:
determining the position of the mobile terminal at the eyes of the person based on repeatedly recording the surroundings of the mobile terminal using the built-in camera of the mobile terminal and repeatedly measuring of the acceleration of the mobile terminal using the built-in acceleration sensor of the mobile terminal during a movement of the mobile terminal to the eyes by the built-in acceleration sensor of the mobile terminal of the person.

12. The method as claimed in claim 11, wherein:
the determination of the near point of the person and the determination of the position of at least one eye of the person is implemented in a stationary coordinate system.

13. The method as claimed in claim 11, further comprising:
requesting the person to move the mobile terminal to the eyes of the person by using output means of the mobile terminal; and
receiving feedback when the mobile terminal is at the eyes of the person by using input means of the mobile terminal.

14. A method for a mobile terminal having a built-in camera, a built-in acceleration sensor, and a processor, for determining a spherical power for a spectacle lens, the method comprising:
determining the near-point distance of the person with the method as claimed in claim 7; and
determining the spherical power on the basis of the near-point distance and a reading distance of the person.

15. The method as claimed in claim 14, wherein the method further comprises:
determining the position of the mobile terminal in the reading position based on repeatedly recording the surroundings of the mobile terminal using the built-in camera of the mobile terminal and repeatedly measuring the acceleration of the mobile terminal using the built-in acceleration sensor of the mobile terminal during a movement of the mobile terminal into the reading position; and
determining the reading distance on the basis of the position of the mobile terminal in the reading position and the position of the eyes.

16. The method as claimed in claim 15, further comprising:
requesting the person to move the mobile terminal into a reading position of the person by using output means of the mobile terminal; and
receiving feedback when the mobile terminal is in the reading position by means of input means of the mobile terminal.

17. A method for producing a spectacle lens, comprising:
determining the spherical power, as claimed in claim 14; and
producing a spectacle lens on the basis of the determined spherical power.

18. A computer program stored on a non-transitory storage medium for a mobile terminal having a camera, an acceleration sensor, input means, and output means, the computer program comprising instructions which, when the computer program is executed by the mobile terminal, cause the method as claimed in claim 1 to be carried out by the mobile terminal.

19. A mobile terminal for determining the near point of a person, the mobile terminal comprising:
a built-in camera;
a built-in acceleration sensor; and
a processor configured so that the mobile terminal carries out the following steps:
performing a movement of the mobile terminal in front of the person;
repeatedly recording surroundings of the mobile terminal by the built-in camera of the mobile terminal, the repeated recordings including at least one object other than the person;
repeatedly measuring an acceleration of the mobile terminal by the built-in acceleration sensor of the mobile terminal during a movement of the mobile terminal to the near point of the person; and
determining the position of the mobile terminal at the near point of the person based on the repeated recordings and the repeated measurements.

20. The mobile terminal as claimed in claim 19, wherein the processor is configured so that the determination of the position of the mobile terminal at the near point is implemented by visual-inertial odometry.

21. The mobile terminal as claimed in claim 19, wherein the processor is configured so that determination of the position of the mobile terminal at the near point is implemented based on a plurality of objects identified in repeated recordings of the surroundings of the mobile terminal.

22. The mobile terminal as claimed in claim 19, wherein the processor is configured so that the determination of the position of the mobile terminal at the near point is implemented as a determination of position in a stationary coordinate system.

23. The mobile terminal as claimed in claim 19, wherein the mobile terminal has a built-in back camera, and wherein the processor is configured so that the repeated recordings are implemented by means of the back camera of the mobile terminal.

24. The mobile terminal as claimed in claim 19, the mobile terminal being further configured for determining the near-point distance of the person, wherein the processor is configured so that the following steps are furthermore carried out by the mobile terminal:
determining the position of at least one eye of the person; and
determining the near-point distance based on the position of the mobile terminal at the near point and the position of the at least one eye,
wherein the determination of the position of the at least one eye comprises:
during the movement of the mobile terminal to the near point of the person, repeatedly determining the position and orientation of the mobile terminal based on the repeated recordings of the surroundings and the repeated measurement of the acceleration, and repeatedly recording an image of the at least one eye of the person using the built-in camera or a further built-in camera of the mobile terminal;
identifying the at least one eye in the images of the at least one eye of the person; and
determining the position of the at least one eye of the person based on the positions and orientations of the mobile terminal and the identified positions of the eyes in the images.

25. The mobile terminal as claimed in claim 19, the mobile terminal being further configured for determining the near-point distance of the person, wherein the processor is configured so that the mobile terminal determines the position of the mobile terminal at the near point in a stationary coordinate system, and
wherein the mobile terminal furthermore carries out the following steps:
determining the position of at least one eye of the person in the stationary coordinate system; and
determining the near-point distance based on the position of the mobile terminal at the near point and the position of the at least one eye,
wherein the determination of the position of the at least one eye of the person comprises:

determining the position of the mobile terminal at the eyes of the person on the basis of repeatedly recording the surroundings of the mobile terminal using the built-in camera of the mobile terminal and repeatedly measuring of the acceleration of the mobile terminal using the built-in acceleration sensor of the mobile terminal during a movement of the mobile terminal to the eyes by the built-in acceleration sensor of the mobile terminal of the person.

26. The mobile terminal as claimed in claim 19, the mobile device being further configured for determining a spherical power for a spectacle lens, wherein the processor is configured so that the mobile terminal determines the position of the mobile terminal at the near point in a stationary coordinate system, and wherein the mobile terminal furthermore is configured to carry out the following steps:

determining the position of at least one eye of the person in the stationary coordinate system, and determining the near-point distance based on the position of the mobile terminal at the near point and the position of the at least one eye; and determining the spherical power on the basis of the near-point distance and a reading distance of the person, wherein the processor is configured so that the mobile terminal carries out the following steps:

determining the position of the mobile terminal in the reading position in the stationary coordinate system on the basis of repeatedly recording the surroundings of the mobile terminal using the built-in camera of the mobile terminal and repeatedly measuring the acceleration of the mobile terminal using the built-in acceleration sensor of the mobile terminal during a movement of the mobile terminal into the reading position; and determining the reading distance on the basis of the position of the mobile terminal in the reading position and the position of the eyes.

27. The mobile terminal as claimed in claim 19, wherein the processor is configured to:

determine the position of the mobile terminal at the near point of the person, wherein the determination of the position of the mobile terminal at the near point is implemented by the processor based on the repeated recordings of surroundings of the mobile terminal by the built-in camera of the mobile terminal and based on the repeated measurement of the acceleration of the mobile terminal by the built-in acceleration sensor of the mobile terminal during the movement of the mobile terminal to the near point.

28. A method for a mobile terminal having a built-in camera, a built-in acceleration sensor, and a processor, for determining a near point of a person, the method comprising:

determining a position of the mobile terminal at the near point of the person, wherein the determination of the position of the mobile terminal at the near point is implemented by the processor based on repeated recordings of surroundings of the mobile terminal by the built-in camera of the mobile terminal and based on a repeated measurement of an acceleration of the mobile terminal by the built-in acceleration sensor of the mobile terminal during a movement of the mobile terminal to the near point, and wherein the built-in camera is a back camera of the mobile terminal, which is arranged on an opposite side of the mobile terminal to a display of the mobile terminal.

29. A mobile terminal for determining the near point of a person, the mobile terminal comprising:

a built-in camera;

a built-in acceleration sensor; and a processor configured so that the mobile terminal carries out the following steps:

determining the position of the mobile terminal at the near point of the person, wherein the determination of the position of the mobile terminal at the near point is implemented based on repeated recordings of surroundings of the mobile terminal by the built-in camera of the mobile terminal and based on a repeated measurement of an acceleration of the mobile terminal by the built-in acceleration sensor of the mobile terminal during a movement of the mobile terminal to the near point, and wherein the mobile terminal further has a built-in back camera, and wherein the processor is configured so that the repeated recordings are implemented by the back camera of the mobile terminal.

* * * * *

UNITED STATES PATENT AND TRADEMARK OFFICE
CERTIFICATE OF CORRECTION

PATENT NO. : 11,867,984 B2
APPLICATION NO. : 18/157454
DATED : January 9, 2024
INVENTOR(S) : Claudius Weimann It is certified that error appears in the above-identified patent and that said Letters Patent is hereby corrected as shown below:

In the Specification

In Column 5, Line 16: change "G. Mitzi et al." to -- G. Nützi et al. --

Signed and Sealed this
Twentieth Day of February, 2024

Katherine Kelly Vidal
*Director of the United States Patent and Trademark Office*